United States Patent
Kim et al.

(10) Patent No.: US 9,011,940 B2
(45) Date of Patent: Apr. 21, 2015

(54) BITTER-TASTE INHIBITOR AND GINSENG COMPOSITION COMPRISING SAME

(75) Inventors: Su Hwan Kim, Yongin-si (KR); Chan Woong Park, Yongin-si (KR); Jin Yeong Shin, Yongin-si (KR); Wan Gi Kim, Yongin-si (KR); Sang Jun Lee, Yongin-si (KR)

(73) Assignee: Amorepacific Corporation (KR)

( * ) Notice: Subject to any disclaimer, the term of this patent is extended or adjusted under 35 U.S.C. 154(b) by 0 days.

(21) Appl. No.: 14/122,916

(22) PCT Filed: May 31, 2012

(86) PCT No.: PCT/KR2012/004299
§ 371 (c)(1),
(2), (4) Date: Nov. 27, 2013

(87) PCT Pub. No.: WO2012/165876
PCT Pub. Date: Dec. 6, 2012

(65) Prior Publication Data
US 2014/0093590 A1    Apr. 3, 2014

(30) Foreign Application Priority Data
May 31, 2011 (KR) .................. 10-2011-0052009

(51) Int. Cl.
*A01N 65/00* (2009.01)
*A23L 1/22* (2006.01)
*A61K 36/258* (2006.01)
*A61K 47/26* (2006.01)

(52) U.S. Cl.
CPC .......... *A23L 1/22075* (2013.01); *A23L 1/22083* (2013.01); *A23V 2002/00* (2013.01); *A61K 36/258* (2013.01); *A61K 47/26* (2013.01)

(58) Field of Classification Search
None
See application file for complete search history.

(56) References Cited

U.S. PATENT DOCUMENTS
5,013,716 A    5/1991   Cherukuri et al.

FOREIGN PATENT DOCUMENTS

| CN | 101828619 | 9/2010 |
|----|-----------|--------|
| KR | 1990-0005890 | 5/1990 |
| KR | 1999-000223 | 1/1999 |
| KR | 1020040004242 A | 1/2004 |
| KR | 10-0832334 | 5/2008 |
| KR | 10-0910176 | 7/2009 |

OTHER PUBLICATIONS

International Search Report—PCT/KR2012/004299 dated Dec. 28, 2012.
Written Opinion—PCT/KR2012/004299 dated Dec. 28, 2012.
KR Office Action—Korean Application No. 10-2011-0052009 issued Sep. 13, 2013 from Korean Patent Office.

(Continued)

*Primary Examiner* — Michael Meller
(74) *Attorney, Agent, or Firm* — Cantor Colburn LLP

(57) ABSTRACT

The present invention relates to a bitter-taste inhibitor containing indigestible maltodextrin, and to a ginseng composition comprising the bitter-taste inhibitor. According to the present invention, the particular bitter taste of ginseng may be eliminated without the loss of a marker component found in ginseng, thereby enabling the easy intake of ginseng.

5 Claims, 2 Drawing Sheets

(56) References Cited

OTHER PUBLICATIONS

Chinese Office Action—CN Application No. 201280033990.8 dated Nov. 18, 2014, citing CN101828619 and "The Mechanism of Bitter Formation and Advances in Studies on Bitter Taste Masking Technology of TCM.", partial translation only.

Liao, et al., "The Mechanism of Bitter Formation and Advances in Studies on Bitter Taste Masking Technology of TCM", Shizhen Medicine and Materia Medica Research, vol. 19, No. 5, 2008, pp. 1276-1278, partial translation only.

BITTER-TASTE INHIBITOR AND GINSENG COMPOSITION COMPRISING SAME

TECHNICAL FIELD

The present disclosure relates to an agent for masking bitterness and a ginseng composition comprising same. More particularly, the present disclosure relates to an agent for masking bitterness comprising indigestible maltodextrin, and a ginseng composition comprising same.

BACKGROUND ART

A number of foods and drinks often taste unpleasantly bitter or sour. Since the taste is very important in consumers' selection of food products, many efforts have been made to mask or reduce the unpleasant taste.

Bitter-tasting materials are water-insoluble in general. Bitterness is characterized in that longer time is required to sense as compared to other sweet, sour and salty tastes and is long-lasting. The representative bitter-tasting substance in root plant such as red ginseng, green tea, etc. is saponin, which is a glycoside composed of a sugar and a carbohydrate. Red ginseng refers to a fresh ginseng which has been steamed and dried. The major components of red ginseng include, like white ginseng, glycosides, panacen, polyacetylene compounds, nitrogen-comprising ingredients, flavonoids, vitamin B, microelements, enzymes, antioxidants, organic acids and amino acids. Many researches have been made on the major components and pharmacological activity of red ginseng. Scientifically proven efficacies of red ginseng include immune-enhancing, anticancer, anticoagulant, blood pressure-lowering, anti-stress, blood sugar-lowering, anti-hyperlipidemic and anti-aging efficacies. According to researches, red ginseng has been shown to improve the body's ability to defend against various harmful environments and stresses and to facilitate recovery from fatigue. Given these pharmacological efficacies of red ginseng, it is expected that long-term intake of red ginseng will be helpful in preventing and reducing the risk of various adult diseases. However, the bitter taste and characteristic flavor of red ginseng make it to be unfavored by children and fastidious people.

At present, cyclodextrins (CD) are used to lodge saponins inside the cyclodextrin rings and thereby masking the bitter taste of red ginseng. As natural plant-derived food additives, although the cyclodextrins are effective in masking the bitter taste of foods, they tend to lower the level of the active ingredients. Accordingly, sugars or sweeteners are used to lower or avoid the use of cyclodextrins.

DISCLOSURE

Technical Problem

The present disclosure is directed to providing an agent for masking bitterness, which provides a superior bitter taste masking effect without loss of active ingredients of ginseng, without addition of additives such as cyclodextrins or sweeteners, and a ginseng composition wherein the characteristic bitter taste of ginseng is masked.

Technical Solution

In one general aspect, the present disclosure provides an agent for masking bitterness, comprising indigestible maltodextrin.

In an exemplary embodiment of the present disclosure, the indigestible maltodextrin may have an average molecular weight of 100-10000.

In an exemplary embodiment of the present disclosure, the agent for masking bitterness may further comprise a citrus extract.

In an exemplary embodiment of the present disclosure, the citrus extract may be comprised in an amount of 0.001-80 parts by weight based on 100 parts by weight of the indigestible maltodextrin.

In another general aspect, the present disclosure provides a ginseng composition comprising the agent for masking bitterness.

In an exemplary embodiment of the present disclosure, the ginseng may be one or more selected from a group consisting of red ginseng, white ginseng, black ginseng, wild ginseng, cultivated wild ginseng and woods-cultivated ginseng.

In an exemplary embodiment of the present disclosure, the ginseng may be a ginseng concentrate having a solid content of at least 60 wt %.

In an exemplary embodiment of the present disclosure, the agent for masking bitterness may be comprised in an amount of 0.001-80 parts by weight based on 100 parts by weight of the composition.

Advantageous Effects

An agent for masking bitterness of the present disclosure allows easy intake of food by masking the bitter taste of the food. And, a ginseng composition comprising the agent for masking bitterness of the present disclosure allows easy intake of ginseng by masking the characteristic bitter taste of ginseng. Accordingly, the ginseng composition with the bitter taste of ginseng masked according to the present disclosure can be used to develop ginseng-comprising health supplements and foods.

BEST MODE

Figure 1:
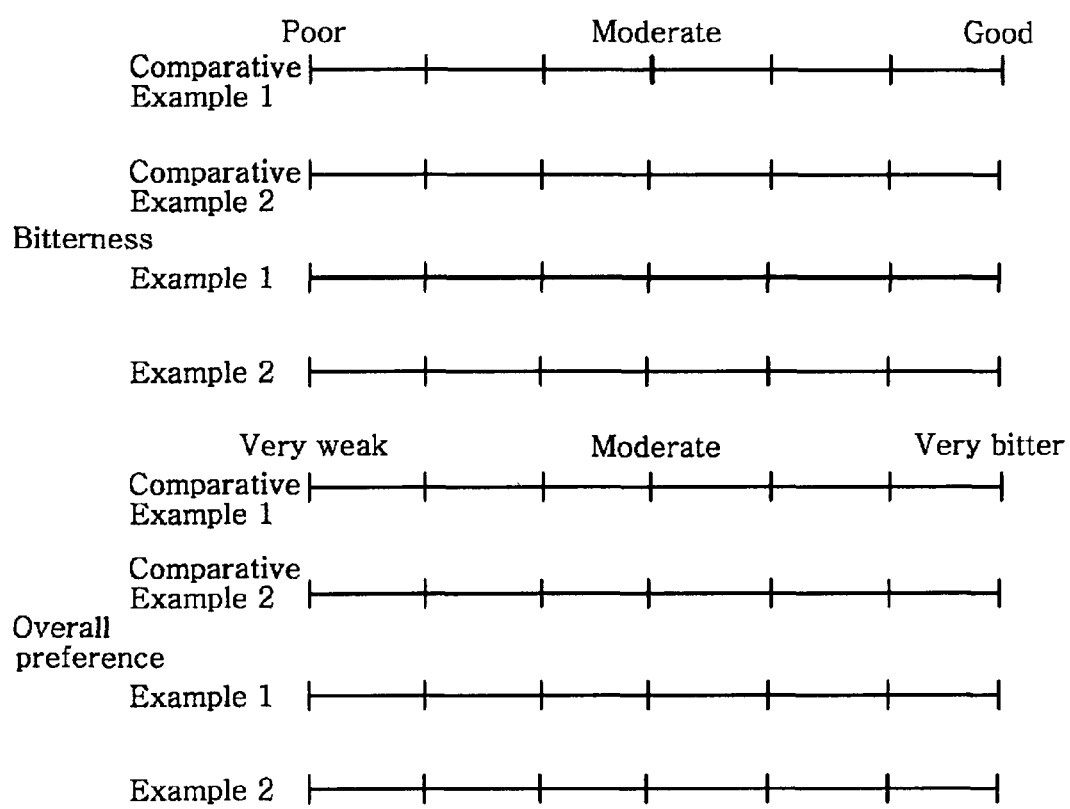
FIG. 1 is a table of sensory evaluation for use in Test Example 1.
Figure 2:
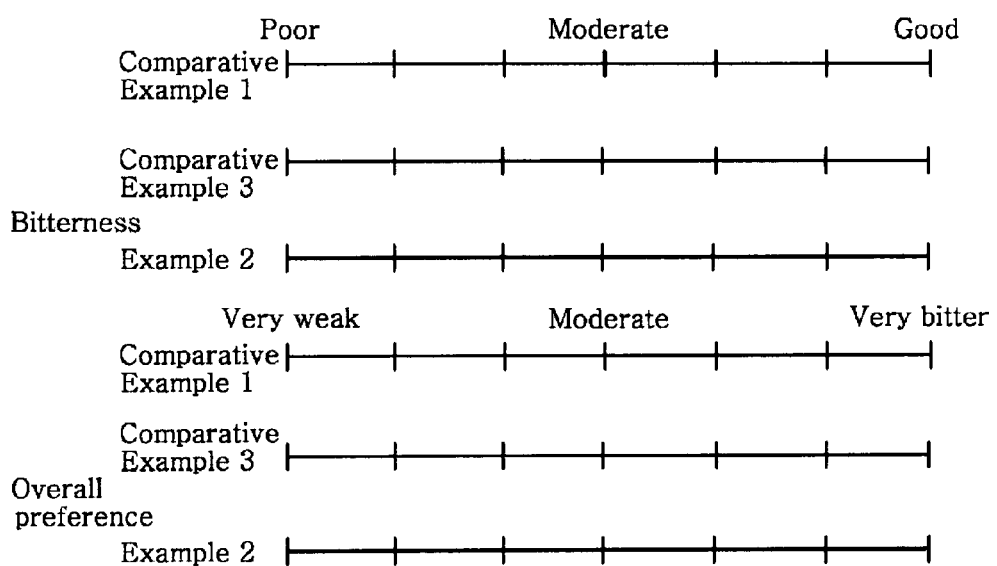
FIG. 2 is a table of sensory evaluation for use in Test Example 2.

Hereinafter, the embodiments of the present disclosure will be described in detail so that those of ordinary skill in the art to which the present disclosure belongs can easily carry out the present disclosure.

The present disclosure provides an agent for masking bitterness comprising indigestible maltodextrin.

The agent for masking bitterness may further comprise a citrus extract. The citrus extract may be comprised in an amount of 0.001-80 parts by weight based on 100 parts by weight of the indigestible maltodextrin. For example, it may be comprised in an amount of 0.001-30 parts by weight, specifically 0.001-10 parts by weight, more specifically 0.1-10 parts by weight. If the citrus extract is comprised in an amount less than 0.001 part by weight, weighing error may occur because the amount is too small. And, if the amount exceeds 80 parts by weight, sweet taste may be too strong.

The present disclosure also provides a ginseng composition comprising the agent for masking bitterness.

The ginseng is not particularly limited, but may be one or more selected from a group consisting of red ginseng, white ginseng, black ginseng, wild ginseng, cultivated wild ginseng and woods-cultivated ginseng. White ginseng refers to a fresh ginseng as it is. Red ginseng refers to a fresh ginseng which has been steamed and dried. During the drying, the color turns fawny to reddish brown due to browning. Black ginseng refers to a ginseng obtained by further steaming and drying red ginseng several times and displaying black color. Wild ginseng refers to a naturally growing ginseng, and cultivated wild ginseng refers to a wild ginseng which has been cultivated. Woods-cultivated ginseng refers to a ginseng which has been cultivated in the woods.

The ginseng may be a ginseng concentrate having a solid content of at least 60 wt %, specifically 60-90 wt %. The solid content standard for the red ginseng concentrate in health supplements is at least 60%, and if the solid content is 90% or higher, processing may be difficult because of unsatisfactory flow property and loss of the concentrate may increase.

The ginseng concentrate may be obtained by a generally employed method without particular limitation. For example, it may be prepared by repeatedly extracting red ginseng root 3-5 times in an extraction solvent such as water and alcohol at 65-75° C. for 9-11 hours, filtering the extract, and concentrating the extract under reduced pressure of 500-700 mmHg at 65-75° C. to a solid content of at least 60%.

The agent for masking bitterness may be comprised in an amount of 0.001-80 parts by weight based on the 100 parts by weight of the composition. For example, it may be comprised in an amount of 0.1-50 parts by weight, specifically 10-35 parts by weight. If the amount is less than 0.001 part by weight, the effect of masking bitter taste may be insufficient. And, if the amount exceeds 80 parts by weight, the efficacy of ginseng may not be fully exerted.

The indigestible maltodextrin is obtained from cornstarch and is used as a raw material in health supplements. Because of its structural features, it is not easily digested by human and has low viscosity, sweetness of 1/10 that of sugar, high transparency and high solubility. The indigestible maltodextrin may have an average molecular weight of about 100-10,000, for example about 1,000-5,000, specifically about 1,500-2,500. The indigestible maltodextrin may have a branched structure. The molecular structure of the indigestible maltodextrin is as follows.

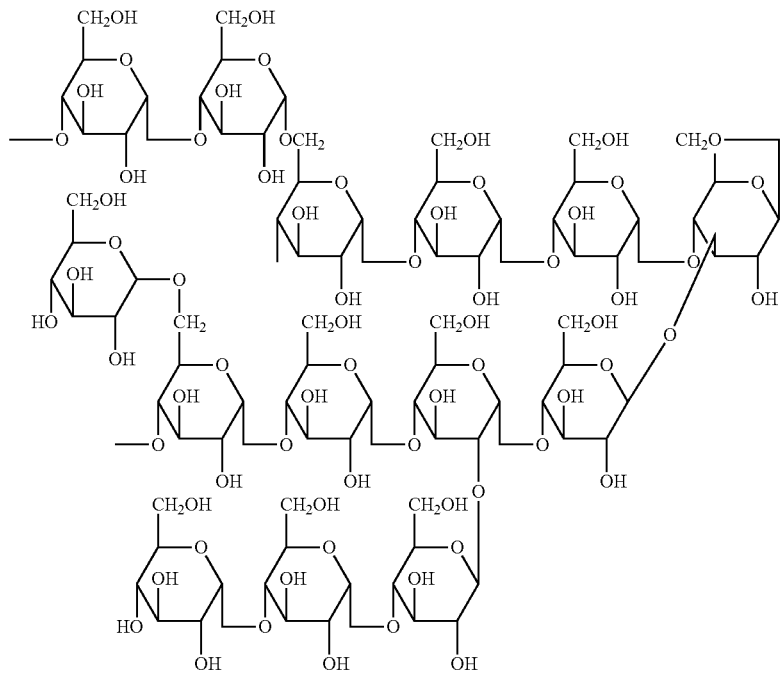

The citrus extract may be derived from citrus plants such as mandarin, tangerine, orange, lemon, etc. or may be synthesized. The citrus used in the present disclosure may be the fruit of any citrus plants, and the citrus extract may be obtained by commonly employed extraction or synthesis methods.

The present disclosure also provides a method for masking the bitter taste of ginseng by adding indigestible maltodextrin to a ginseng concentrate. The method may further include adding a citrus extract to the ginseng concentrate.

The ginseng concentrate with the indigestible maltodextrin and the citrus extract added is superior in terms of sensation as compared to the existing ginseng drinks or ginseng concentrates.

Hereinafter, the present disclosure will be described in detail through examples. However, the following examples are for illustrative purposes only and it will be apparent to those of ordinary skill in the art that the scope of the present disclosure is not limited by the examples.

Example 1

500 g of red ginseng was repeatedly extracted 4 times in 1.5 L of an extraction solvent (water:alcohol=1:1 (vol/vol)) at 70° C. for 10 hours, and the resulting extract was pressure-filtered through a 250-mesh filter. The resulting filtrate was concentrated under reduce pressure of 600 mmHg at 70° C. to a solid content of at least 60%, and the resulting concentrate was steam-sterilized at 83° C. for 20 minutes to obtain a red ginseng concentrate (Rg1+Rb1=10 mg/g).

10 g of the prepared red ginseng concentrate was mixed with 25 g of indigestible maltodextrin.

Example 2

10 g of the prepared red ginseng concentrate which was prepared in the same manner as in Example 1 was mixed with 25 g of indigestible maltodextrin and 0.1 g of citrus extract (Flavex Technology).

Comparative Example 1

500 g of red ginseng was repeatedly extracted 4 times in 1.5 L of an extraction solvent (water:alcohol=1:1 (vol/vol)) at 70° C. for 10 hours, and the resulting extract was pressure-filtered through a 250-mesh filter. The resulting filtrate was concentrated under reduce pressure of 600 mmHg at 70° C. to a solid content of at least 60%, and the resulting concentrate was steam-sterilized at 83° C. for 20 minutes to obtain a red ginseng concentrate (Rg1+Rb1=10 mg/g).

Comparative Example 2

A white ginseng concentrate (Rg1+Rb1=10 mg/g) was prepared in a substantially same manner as in Comparative Example 1, except that white ginseng was used instead of red ginseng.

Comparative Example 3

10 g of the red ginseng concentrate prepared in Comparative Example 1 was mixed with 25 g of cyclodextrin.

Test Example 1

Sensory Evaluation

Sensory evaluation of the samples of the concentrates prepared in Examples 1-2 and Comparative Examples 1-2 was conducted by twenty well-trained panels on bitterness and preference.

The concentrates prepared in Examples 1-2 and Comparative Examples 1-2 were dissolved in water to a total weight of 100 g. The panels were asked to make evaluation based on the following 7-score scale. The result of sensory evaluation on bitterness and overall preference is shown in Table 1.

TABLE 1

| Sample No. | Comparative Example 1 | Comparative Example 2 | Example 1 | Example 2 |
|---|---|---|---|---|
| Bitterness | 6.42 | 6.75 | 5.45 | 3.26 |
| Overall preference | 3.64 | 3.54 | 4.22 | 5.02 |

As seen from Table 1, the sample of Example 2 showed the best result in masking of bitterness and overall preference. The result was significant in 95% level. The sample of Example 1 showed the next best result. Accordingly, it can be seen that addition of the indigestible maltodextrin or the indigestible maltodextrin and the citrus extract to ginseng-comprising health supplements is effective in masking the bitter taste of ginseng.

Test Example 2

Sensory Evaluation and Measurement of Active Ingredients

Sensory evaluation was conducted by twenty well-trained panels on bitterness and preference.

The concentrates prepared in Example 2 and Comparative Examples 1 and 3 were dissolved in water to a total weight of 100 g. The panels were asked to make evaluation based on the following 7-score scale. The result of sensory evaluation on bitterness and overall preference is shown in Table 2.

In addition, the active ingredients (Rg1+Rb1) comprised in each sample were measured according to the guideline of Korean Food Standards Codex. The result is also shown in Table 2.

TABLE 2

| Sample No. | | Comparative Example 1 | Comparative Example 3 | Example 2 |
|---|---|---|---|---|
| Bitterness | | 6.50 | 1.52 | 4.02 |
| Overall preference | | 3.02 | 6.84 | 5.62 |
| Active ingredients | Before masking | 9.9 mg/10 g | 9.9 mg/10 g | 9.9 mg/10 g |
| | After masking | 9.6 mg/10 g | 2.2 mg/10 g | 9.5 mg/10 g |

As seen from Table 2, the sample of Comparative Example 3 showed the best result in masking of bitterness and overall preference. However, when the bitter taste was masked using cyclodextrin (Comparative Example 3), the content of the active ingredients was decreased by about 78%. This is why cyclodextrin is not currently used to mask bitterness in ginseng products. The sample of Example 2 showed the next best result in masking of bitterness and overall preference. It was confirmed that the bitter taste can be masked without loss of the active ingredients by using the indigestible maltodextrin and the citrus extract. Accordingly, it can be seen that addition of the indigestible maltodextrin and the citrus extract to ginseng-comprising health supplements is effective in masking the bitter taste of ginseng.

The invention claimed is:

1. A method for masking bitterness in a food having bitterness comprising adding a composition consisting essentially of an indigestible maltodextrin, and a citrus extract to said food which masks the bitterness in the food,
   wherein the food comprises a ginseng extract, and
   wherein said ginseng extract is selected from the group consisting of red ginseng, white ginseng, black ginseng, wild ginseng, cultivated wild ginseng and woods cultivated ginseng.

2. The method for masking bitterness in a food having bitterness according to claim 1, wherein the ginseng extract is a ginseng concentrate having a solid content of at least 60 wt %.

3. The method for masking bitterness in a food having bitterness according to claim 1, wherein the indigestible maltodextrin is in an amount of 0.001-80 parts by weight based on 100 parts by weight of the composition.

4. The method for masking bitterness in a food having bitterness according to claim 1, wherein the indigestible maltodextrin has an average molecular weight of 100-10000.

5. The method for masking bitterness in a food having bitterness according to claim 1, wherein the citrus extract is in an amount of 0.001-80 parts by weight based on 100 parts by weight of the indigestible maltodextrin.

* * * * *